United States Patent

Wyss et al.

(10) Patent No.: US 9,119,723 B2
(45) Date of Patent: Sep. 1, 2015

(54) POSTERIOR STABILIZED ORTHOPAEDIC PROSTHESIS ASSEMBLY

(75) Inventors: Joseph G. Wyss, Fort Wayne, IN (US); Travis D. Bennett, Huntington, IN (US)

(73) Assignee: DEPUY (IRELAND) (IE)

( * ) Notice: Subject to any disclaimer, the term of this patent is extended or adjusted under 35 U.S.C. 154(b) by 569 days.

(21) Appl. No.: 13/534,459

(22) Filed: Jun. 27, 2012

(65) Prior Publication Data

US 2013/0006372 A1 Jan. 3, 2013

Related U.S. Application Data

(63) Continuation-in-part of application No. 13/527,758, filed on Jun. 20, 2012, now Pat. No. 8,734,522, which is a continuation of application No. 12/165,582, filed on Jun. 30, 2008, now Pat. No. 8,206,451.

(60) Provisional application No. 61/503,348, filed on Jun. 30, 2011.

(51) Int. Cl.
*A61F 2/38* (2006.01)
(52) U.S. Cl.
CPC .............. *A61F 2/3886* (2013.01); *A61F 2/3868* (2013.01)
(58) Field of Classification Search
CPC .............................. A61F 2/3868; A61F 2/3886
USPC .......... 623/20.21, 20.27, 20.29, 20.32, 20.14, 623/20.24, 20.31
See application file for complete search history.

(56) References Cited

U.S. PATENT DOCUMENTS

| | | | |
|---|---|---|---|
| 3,765,033 A | 10/1973 | Goldberg et al. |
| 3,840,905 A | 10/1974 | Deane |
| 3,852,045 A | 12/1974 | Wheeler |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |
| 4,209,861 A | 7/1980 | Walker et al. |

(Continued)

FOREIGN PATENT DOCUMENTS

| | | |
|---|---|---|
| CN | 1803106 A | 7/2006 |
| CN | 1872009 A | 12/2006 |

(Continued)

OTHER PUBLICATIONS

Biomet, Vanguard Mono-Lock Tibial System, Patented Convertible Tibial Bearing Technology, 2009, 2 Pages.

(Continued)

*Primary Examiner* — David H Willse
*Assistant Examiner* — Javier Blanco
(74) *Attorney, Agent, or Firm* — Barnes & Thornburg LLP

(57) ABSTRACT

A posterior stabilized knee orthopaedic prosthesis assembly includes a tibial bearing, a primary femoral component, and a revision femoral component. Each of the primary and revision femoral components is configured to separately articulate with the tibial bearing. However, each of the primary and revision femoral components has different geometry. The primary femoral component includes a posterior cam having a posterior cam surfacing including a concave cam surface and a convex cam surface. The revision femoral component includes a posterior cam having only a convex cam surface.

11 Claims, 9 Drawing Sheets

(56) References Cited

U.S. PATENT DOCUMENTS

| | | |
|---|---|---|
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |
| 4,612,160 A | 9/1986 | Donlevy |
| 4,673,407 A | 6/1987 | Martin |
| 4,714,474 A | 12/1987 | Brooks, Jr. |
| 4,795,468 A | 1/1989 | Hodorek |
| 4,808,185 A | 2/1989 | Penenberg et al. |
| 4,822,362 A | 4/1989 | Walker |
| 4,838,891 A | 6/1989 | Branemark |
| 4,888,021 A | 12/1989 | Forte et al. |
| 4,938,769 A | 7/1990 | Shaw |
| 4,944,757 A | 7/1990 | Martinez |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne |
| 5,007,933 A | 4/1991 | Sidebotham et al. |
| 5,011,496 A | 4/1991 | Forte et al. |
| 5,019,103 A | 5/1991 | Van Zile |
| 5,037,423 A | 8/1991 | Kenna |
| 5,071,438 A | 12/1991 | Jones et al. |
| 5,080,675 A | 1/1992 | Lawes |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin |
| 5,258,044 A | 11/1993 | Lee |
| 5,271,737 A | 12/1993 | Baldwin |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker |
| 5,330,534 A | 7/1994 | Herrington et al. |
| 5,344,460 A | 9/1994 | Turanyi et al. |
| 5,344,461 A | 9/1994 | Phlipot |
| 5,344,494 A | 9/1994 | Davidson |
| 5,358,527 A | 10/1994 | Forte |
| 5,368,881 A | 11/1994 | Kelman |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun |
| 5,449,745 A | 9/1995 | Sun |
| 5,458,637 A | 10/1995 | Hayes |
| 5,480,446 A | 1/1996 | Goodfellow |
| 5,543,471 A | 8/1996 | Sun |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun |
| 5,658,333 A | 8/1997 | Kelman |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier |
| 5,702,464 A | 12/1997 | Lackey et al. |
| 5,702,466 A | 12/1997 | Pappas et al. |
| 5,725,584 A | 3/1998 | Walker et al. |
| 5,728,748 A | 3/1998 | Sun |
| 5,732,469 A | 3/1998 | Hamamoto |
| 5,755,800 A | 5/1998 | O'Neil |
| 5,755,801 A | 5/1998 | Walker et al. |
| 5,755,803 A | 5/1998 | Haines et al. |
| 5,765,095 A | 6/1998 | Flak |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow |
| 5,871,546 A | 2/1999 | Colleran et al. |
| 5,879,394 A | 3/1999 | Ashby |
| 5,879,400 A | 3/1999 | Merrill |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman |
| 5,964,808 A | 10/1999 | Blaha |
| 5,976,147 A | 11/1999 | LaSalle et al. |
| 5,984,969 A | 11/1999 | Matthews |
| 5,989,027 A | 11/1999 | Wagner |
| 5,997,577 A | 12/1999 | Herrington et al. |
| 6,004,351 A | 12/1999 | Tomita et al. |
| 6,005,018 A | 12/1999 | Cicierega |
| 6,010,534 A | 1/2000 | O'Neil et al. |
| 6,013,103 A | 1/2000 | Kaufman et al. |
| 6,017,975 A | 1/2000 | Saum |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal Or |
| 6,068,658 A | 5/2000 | Insall |
| 6,080,195 A | 6/2000 | Colleran et al. |
| 6,090,144 A | 7/2000 | Letot |
| 6,123,728 A | 9/2000 | Brosnahan |
| 6,123,729 A | 9/2000 | Insall et al. |
| 6,123,896 A | 9/2000 | Meeks, III |
| 6,126,692 A | 10/2000 | Robie et al. |
| 6,135,857 A | 10/2000 | Shaw |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun |
| 6,206,926 B1 | 3/2001 | Pappas |
| 6,210,444 B1 | 4/2001 | Webster |
| 6,210,445 B1 | 4/2001 | Zawadzki |
| 6,217,618 B1 | 4/2001 | Hileman |
| 6,228,900 B1 | 5/2001 | Shen |
| 6,238,434 B1 | 5/2001 | Pappas |
| 6,242,507 B1 | 6/2001 | Saum |
| 6,245,276 B1 | 6/2001 | McNulty |
| 6,258,127 B1 | 7/2001 | Schmotzer |
| 6,264,697 B1 | 7/2001 | Walker |
| 6,280,476 B1 | 8/2001 | Metzger |
| 6,281,264 B1 | 8/2001 | Salovey |
| 6,299,646 B1 | 10/2001 | Chambat et al. |
| 6,316,158 B1 | 11/2001 | Saum |
| 6,319,283 B1 | 11/2001 | Insall |
| 6,325,828 B1 | 12/2001 | Dennis et al. |
| 6,344,059 B1 | 2/2002 | Krakovits et al. |
| 6,361,564 B1 | 3/2002 | Marceaux |
| 6,372,814 B1 | 4/2002 | Sun |
| 6,379,388 B1 | 4/2002 | Ensign et al. |
| 6,428,577 B1 | 8/2002 | Evans et al. |
| 6,443,991 B1 | 9/2002 | Running |
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot |
| 6,506,216 B1 | 1/2003 | McCue |

(56) References Cited

U.S. PATENT DOCUMENTS

| | | |
|---|---|---|
| 6,524,522 B2 | 2/2003 | Vaidyanathan |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee |
| 6,589,283 B1 | 7/2003 | Metzger et al. |
| 6,592,787 B2 | 7/2003 | Pickrell |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre |
| 6,664,308 B2 | 12/2003 | Sun |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun |
| 6,846,327 B2 | 1/2005 | Khandkar |
| 6,846,329 B2 | 1/2005 | McMinn |
| 6,849,230 B1 | 2/2005 | Feichtinger |
| 6,852,272 B2 | 2/2005 | Artz |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram |
| 7,160,330 B2 | 1/2007 | Axelson, Jr. et al. |
| 7,175,665 B2 | 2/2007 | German |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burseein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,206,451 B2 | 6/2012 | Wyss et al. |
| 8,236,061 B2 | 8/2012 | Heldreth et al. |
| 2002/0138150 A1 | 9/2002 | Leclercq |
| 2003/0009232 A1 | 1/2003 | Metzger et al. |
| 2003/0035747 A1 | 2/2003 | Anderson |
| 2003/0044301 A1 | 3/2003 | Lefebvre |
| 2003/0075013 A1 | 4/2003 | Grohowski |
| 2003/0139817 A1 | 7/2003 | Tuke |
| 2003/0153981 A1 | 8/2003 | Wang |
| 2003/0171820 A1 | 9/2003 | Wilshaw |
| 2003/0199985 A1 | 10/2003 | Masini |
| 2003/0212161 A1 | 11/2003 | McKellop |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen |
| 2004/0186583 A1 | 9/2004 | Keller |
| 2004/0215345 A1 | 10/2004 | Perrone |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier |
| 2005/0059750 A1 | 3/2005 | Sun |
| 2005/0069629 A1 | 3/2005 | Becker |
| 2005/0096747 A1 | 5/2005 | Tuttle et al. |
| 2005/0100578 A1 | 5/2005 | Schmid |
| 2005/0123672 A1 | 6/2005 | Justin |
| 2005/0143832 A1 | 6/2005 | Carson |
| 2005/0154472 A1 | 7/2005 | Afriat |
| 2005/0203631 A1 | 9/2005 | Daniels |
| 2005/0209701 A1 | 9/2005 | Suguro et al. |
| 2005/0209702 A1 | 9/2005 | Todd |
| 2005/0249625 A1 | 11/2005 | Bram |
| 2005/0278035 A1 | 12/2005 | Wyss et al. |
| 2006/0002810 A1 | 1/2006 | Grohowski |
| 2006/0015185 A1 | 1/2006 | Chambat et al. |
| 2006/0036329 A1 | 2/2006 | Webster |
| 2006/0052875 A1 | 3/2006 | Bernero |
| 2006/0100714 A1 | 5/2006 | Ensign |
| 2006/0178749 A1 | 8/2006 | Pendleton et al. |
| 2006/0195195 A1 | 8/2006 | Burstein |
| 2006/0228247 A1 | 10/2006 | Grohowski |
| 2006/0231402 A1 | 10/2006 | Clasen |
| 2006/0241781 A1 | 10/2006 | Brown |
| 2006/0257358 A1 | 11/2006 | Wen |
| 2006/0271191 A1 | 11/2006 | Hermansson |
| 2006/0289388 A1 | 12/2006 | Yang |
| 2007/0061014 A1 | 3/2007 | Naegerl |
| 2007/0073409 A1 | 3/2007 | Cooney |
| 2007/0078521 A1 | 4/2007 | Overholser |
| 2007/0100463 A1 | 5/2007 | Aram |
| 2007/0129809 A1 | 6/2007 | Meridew |
| 2007/0135926 A1 | 6/2007 | Walker |
| 2007/0173948 A1 | 7/2007 | Meridew |
| 2007/0196230 A1 | 8/2007 | Hamman |
| 2007/0203582 A1 | 8/2007 | Campbell |
| 2007/0219639 A1 | 9/2007 | Otto et al. |
| 2007/0293647 A1 | 12/2007 | McKellop |
| 2008/0004708 A1 | 1/2008 | Wyss |
| 2008/0021566 A1 | 1/2008 | Peters et al. |
| 2008/0091272 A1 | 4/2008 | Aram |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Savage |
| 2008/0195108 A1 | 8/2008 | Bhatnagar et al. |
| 2008/0199720 A1 | 8/2008 | Liu |
| 2008/0206297 A1 | 8/2008 | Roeder |
| 2008/0269596 A1 | 10/2008 | Revie et al. |
| 2009/0043396 A1 | 2/2009 | Komistek |

(56) References Cited

U.S. PATENT DOCUMENTS

| | | |
|---|---|---|
| 2009/0048680 A1 | 2/2009 | Naegerl |
| 2009/0082873 A1 | 3/2009 | Hazebrouck |
| 2009/0084491 A1 | 4/2009 | Uthgenannt |
| 2009/0088859 A1 | 4/2009 | Hazebrouck et al. |
| 2009/0125114 A1 | 5/2009 | May et al. |
| 2009/0192610 A1 | 7/2009 | Case |
| 2009/0265012 A1 | 10/2009 | Engh et al. |
| 2009/0265013 A1 | 10/2009 | Mendell |
| 2009/0292365 A1 | 11/2009 | Smith |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0063594 A1 | 3/2010 | Hazebrouck |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |
| 2011/0029090 A1 | 2/2011 | Zannis |
| 2011/0029092 A1 | 2/2011 | Deruntz |
| 2011/0035017 A1 | 2/2011 | Deffenbaugh |
| 2011/0035018 A1 | 2/2011 | Deffenbaugh |
| 2011/0106268 A1 | 5/2011 | Deffenbaugh |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0239158 A1 | 9/2012 | Wagner et al. |
| 2012/0259417 A1 | 10/2012 | Wyss et al. |
| 2012/0271428 A1 | 10/2012 | Heldreth et al. |
| 2012/0296437 A1 | 11/2012 | Wyss et al. |
| 2013/0006372 A1 | 1/2013 | Wyss et al. |
| 2013/0006373 A1 | 1/2013 | Wyss et al. |

FOREIGN PATENT DOCUMENTS

| | | |
|---|---|---|
| DE | 4308563 A1 | 9/1994 |
| DE | 19529824 A1 | 2/1997 |
| EP | 510178 | 5/1992 |
| EP | 495340 A1 | 7/1992 |
| EP | 634155 | 1/1995 |
| EP | 636352 A2 | 2/1995 |
| EP | 732091 A2 | 9/1996 |
| EP | 883388 | 12/1998 |
| EP | 634156 B1 | 5/1999 |
| EP | 1129676 | 9/2001 |
| EP | 636352 B1 | 1/2002 |
| EP | 1196118 | 4/2002 |
| EP | 765645 B1 | 8/2003 |
| EP | 1374805 | 1/2004 |
| EP | 1421918 A1 | 5/2004 |
| EP | 1440675 | 7/2004 |
| EP | 1470801 | 10/2004 |
| EP | 732092 B1 | 2/2005 |
| EP | 1518521 A2 | 3/2005 |
| EP | 1226799 B1 | 5/2005 |
| EP | 1591082 A2 | 11/2005 |
| EP | 1779812 A1 | 5/2007 |
| EP | 1923079 A1 | 5/2008 |
| EP | 2649965 | 10/2013 |
| FR | 2417971 | 2/1979 |
| FR | 2621243 | 4/1989 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 A | 4/1967 |
| GB | 2293109 A | 3/1996 |
| GB | 2335145 A | 9/1999 |
| JP | 62205201 | 9/1987 |
| JP | 8500992 T | 2/1996 |
| JP | H08-503407 A | 4/1996 |
| JP | H08-224263 | 9/1996 |
| JP | 2002291779 | 10/2002 |
| JP | 2004167255 | 6/2004 |
| JP | 2006015133 | 1/2006 |
| WO | 7900739 | 10/1979 |
| WO | 8906947 | 8/1989 |
| WO | 9014806 A1 | 12/1990 |
| WO | 9601725 | 1/1996 |
| WO | 9623458 | 8/1996 |
| WO | 9624311 | 8/1996 |
| WO | 9624312 | 8/1996 |
| WO | 9846171 | 10/1998 |
| WO | 9927872 | 6/1999 |
| WO | 9966864 A1 | 12/1999 |
| WO | 0209624 A1 | 2/2002 |
| WO | 03039609 A1 | 5/2003 |
| WO | 03101647 A2 | 12/2003 |
| WO | 2004058108 A1 | 7/2004 |
| WO | 2004069104 | 8/2004 |
| WO | 2005009489 A2 | 2/2005 |
| WO | 2005009729 A2 | 2/2005 |
| WO | 2005072657 A1 | 8/2005 |
| WO | 2005087125 | 9/2005 |
| WO | 2006014294 A1 | 2/2006 |
| WO | 2006130350 A2 | 12/2006 |
| WO | 2007106172 | 9/2007 |
| WO | 2007106172 A | 9/2007 |
| WO | 2007108804 A1 | 9/2007 |
| WO | 2007119173 | 10/2007 |
| WO | 2008100784 A2 | 8/2008 |
| WO | 2009046212 A2 | 4/2009 |
| WO | 2009128943 A2 | 10/2009 |

OTHER PUBLICATIONS

Cari Zeiss, Zeiss Surfcomm 5000—"Contour and Surface Measuring Machines", 2005, 16 pages.
DePuy Inc., "AMK Total Knee System Product Brochure", 1996, 8 pages.
DePuy Knees International, "Sigma CR Porocoat®," 1 page.
DePuy Orthopaedics, Inc., "AMK Total Knee System Legent II Surgical Techinque", 1998, 30 pages.
DePuy Orthopaedics, Inc., "Sigma Fixed Bearing Knees—Function with Wear Resistance", 2010, 0612-65-508 (Rev. 1) 20 pages.
DePuy PFC Sigma RP, "PFC Sigma Knee System with Rotating Platform Technical Monograph", 1999, 0611-29-050 (Rev. 3), 70 pages.
Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages.
European Search Report for European Patent Application No. 09164245.4-2310, Oct. 15, 2009, 5 pgs.
European Search Report for European Patent Application No. 08253140.1-2310, Dec. 23, 2008, 7 pgs.
European Search Report for European Patent Application No. 11150648.1-2310, Apr. 7, 2011, 4 pages.

(56) References Cited

OTHER PUBLICATIONS

European Search Report for European Patent Application No. 06739287.8-2310, Mar. 16, 2010, 3 Pages.
European Search Report for European Patent Application No. 09164478.1-2310, Oct. 20, 2009, 6 Pages.
European Search Report for European Patent Application No. 09164478.1-2310, Apr. 28, 2010, 12 Pages.
European Search Report for European Patent Application No. 10162138.1, Aug. 30, 2010, 7 Pages.
Japanese Search Report for Japanese Patent Application No. 2009-501393, Oct. 26, 2010, 5 Pages.
PCT Notification Concerning Transmittal of International Prel. Report For Corresponding International App. No. PCT/ US2006/010431, Jun. 5, 2007, 89 Pages.
Procedure, References Guide for Use with P.F.C. Sigma Knee Systems, 1998, 8 pages.
Signus Medizintechnik, "PEEK-OPTIMA®, The Polymer for Implants, Technical Information for the Medical Professional", 7 pages.
The Effects of Conformity and Load in Total Knee Replacement, Kuster, et al, Clinical Orthopaedics and Related Research No. 375, Jun. 2000.
Zimmer Nexgen Trabecular Metal Tibial Tray, The Best Thing Next to Bone, 97-5954-001-00, 2007, 4 pages.
Zimmer, Trabecular Metal Monoblock Tibial Components, An Optimal Combination of Material and Design, www.zimmer.com, 2009, 3 pages.
European Search Report for European Patent Application No. 09164235.5-1526, Dec. 22, 2009, 6 pgs.
European Search Report for European Patent Application No. 09164168.8-1526, Jan. 4, 2010, 6 pgs.
PCT Notification Concerning Transmittal of the International Search Report and the Written Opinion of the International Searching Authority, or the Declaration for Corresponding International App. Search Report PCT/US12/44356, Sep. 24, 2012, 3 pages.
PCT Written Opinion of the International Searching Authority for Corresponding International App. Search Report PCT/ US12/44354, Sep. 24, 2012, 11 pages.
Chinese Search Report, Chinese Patent Application No. 200910166935.6, Mar. 26, 2013, 2 pages.
Kessler et al., "Sagittal curvature of total knee replacements predicts in vivo kinematics," Clinical Biomechanics 22(1): 52-58, 2007.
Wang et al., "Biomechanical differences exhibited during sit-to-stand between total knee arthroplasty designs of varying radii," J Arthroplsaty 21(8): 1196-9, 2006.
Saari et al., "The effect of tibial insert design on rising from a chair; motion analysis after total knee replacement," Clin Biomech 19(9): 951-6, 2004.
Ranawat, "Design may be counterproductive for optimizing flexion after TKR," Clin Orthop Rel Res 416: 174-6, 2003.
D'Lima et al., "Quadriceps moment arm and quadriceps forces after total knee arthroplasty," Clin Orthop Rel Res 393:213-20, 2001.
Uvehammer et al., "In vivo kinematics of total knee arthroplasty: flat compared with concave tibial joint surface," J Orthop Res 18(6): 856-64, 2000.
Dennis et al., "In vivo anteroposterior femorotibial translation of total knee arthroplasty: a multicenter analysis," Clin Orthop Rel Res, 356: 47-57, 1998.
Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.
Wang et al., "A biomechanical comparison between the single-axis and multi-axis total knee arthroplasty systems for stand-to-sit movement," Clin Biomech 20(4): 428-33, 2005.
Dennis et al., "Multicenter Determination of In Vivo Kinematics After Total Knee Arthroplasty," Clin. Orthop. Rel. Res., 416, 37-57, 21 pgs.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
Suggs et al., "Three-Dimensional Tibiofemoral Articular Contact Kinematics of a Cruciate-Retaining Total Knee Arthroplasty," JBJS-Am, vol. 88, No. 2, 2006, 10 pgs.
Dennis et al., "In Vivo Determination of Normal and Anterior Cruciate Ligament-Deficient Knee Kinematics," J. Biomechanics, 38, 241-253, 2005, 13 pgs.
Li et al., "Anterior Cruciate Ligament Deficiency Alters the In Vivo Motion of the Tibiofemoral Cartilage Contact Points in Both Anteroposterior and Mediolateral Directions," JBJS-Am, vol. 88, No. 8, Aug. 2006, 10 pgs.
Ries, "Effect of ACL Sacrifice, Retention, or Substitution on K After TKA," http://www.orthosupersite.com/view.asp?rID=23134, Aug. 2007, 5 pgs.
Ferris, "Matching observed spiral form curves to equations of spirals in 2-D images," The First Japanese-Australian Joint Seminar, 7 pgs.
Goodfellow et al., "The Mechanics of the Knee and Prosthesis Design," The Journal of Bone and Joint Surgery, vol. 60-B, No. 3, 12 pgs.
"Vanguard Complete Knee System," Biomet, available at: http://www.biomet.com/patients/vanguard_complete.cfm, downloaded on Feb. 2009, (3 pages).
"NexGen Complete Knee Solution Cruciate Retaining Knee (CR)," Zimmer, available at: http://zimmer.com.au/ctl?template=PC&op=global&action=&template=PC&id=356, downloaded on Feb. 18, 2009, (1 page).
Scorpio Knee TS Single Axis Revision Knee System, Stryker Orthopaedics, http://www.stryker.com/stellent/groups/public/documents/web_prod/023609.pdf, (6 pages).
P. Johal et al, "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).
Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, (4 pages).
Asano et al. "In Vivo Three-Dimensional Knee Kinematics Using a Biplanar Image-Matching Technique," Clin Orthop Rel Res, 388: 157-166, 2001, (10 pages).
European search report; European Application No. 10174439.9-1526; Dec. 20, 2010; 4 pages.
European Search Report for European Patent Application No. 11150648.1-2310, Apr. 7, 2011, 5 Pgs.
Shaw et al., "The Longitudinal Axis of the Knee and the Role of the Cruciate Ligaments in Controlling Transverse Rotation", J.Bone Joint Surg. Am. 1974:56:1603-1609, 8 Pages.
Kurosawa, et al., "Geometry and Motion of the Knee for Implant and Orthotic Design", The Journal of Biomechanics 18 (1985), pp. 487-499, 12 Pages.
Barnes, C.L., et al, "Kneeling Is Safe for Patients Implanted With Medical-Pivot Total Knee Arthoplasty Designs, Journal of Arthoplasty", vol. 00, No. 0 2010, 1-6, 6 Pages.
Blaha, et al., "Kinematics of the Human Knee Using an Open Chain Cadaver Model", Clinical Orthopaedics and Related Research, vol. 410 (2003); 25-34, 10 Pages.
Dennis, et al. "A Multi-Center Analysis of Axial Femorotibial Rotation After Total Knee Arthoplasty", Clinical Orthopaedics 428 (2004); 180-189, 10 Pages.
Fan, Cheng-Yu, et al., "Primitive Results After Medical-Pivot Knee Arthroplasties: A Minimum 5 Year Follow-up Study", The Journal of Arthroplasty, vol. 25, No. 3 2010, 492-496, 5 Pages.
Freeman, M.A.R., et al., "The Movement of the Normal Tibio-Femoral Joint", The Journal of Biomechanics 38 (2005) (2), pp. 197-208, 12 Pgs.

(56) References Cited

OTHER PUBLICATIONS

Fuller, et al., "A Comparison of Lower-Extremity Skeletal Kinematics Measured Using Skin and Pin-Mounted Markers", Human Movement Science 16 (1997) 219-242, 24 Pages.
Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 Pages.
Karachalios, et al., "A Mid-Term Clinical Outcome Study of the Advance Medial Pivot Knee Arthroplasty", www.sciencedirect.come, The Knee 16 (2009); 484-488, 5 Pages.
Komistek, et al., "In Vivo Flouroscopic Analysis of the Normal Human Knee", Clinical Orthopaedics 410 (2003): 69-81, 13 Pages.
Komistek, et al., "In Vivo Polyethylene Bearing Mobility Is Maintained in Posterior Stabilized Total Knee Arthroplasty", Clinical Orthopaedics 428 (2004): 207-213, 7 Pages.
Koo, et al., "The Knee Joint Center of Rotation Is Predominantly on the Lateral Side During Normal Walking", Journal of Biomechanics, vol. 41 (2008): 1269-1273, 5 Pages.
Mannan, et al., "The Medical Rotation Total Knee Replacement: A Clinical and Radiological Review at a Mean Follow-up of Six Years", The Journal of Bone and Joint Surgery, vol. 91-B, No. 6 (Jun. 2009): 750-756, 7 Pages.
Moonot, et al., "Correlation Between the Oxford Knee and American Knee Society Scores at Mid-Term Follow-up", The Journal of Knee Surgery, vol. 22, No. 3 (Jul. 2009), 226-230, 5 Pages.
Murphy, Michael Charles, "Geometry and the Kinematics of the Normal Human Knee", Submitted to Masachusetts Institute of Technology (1990), 379 Pages.
Nakagawa, et al., "Tibiofemoral Movement 3: Full Flexion of the Normal Human Knee", J.Bone Joint Surg. Am, vol. 82-B, No. 8 (2000). 1199-1200, 2 Pages.
Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 Pages.
Shakespeare, et al., "Flexion After Total Knee Replacement. A Comparison Between the Medical Pivot Knee and a Posterior Stabilised Knee", www.sciencedirect.com, The Knee 13 (2006): 371-372, 3 Pages.
Walker, et al., "Motion of a Mobile Bearing Knee Allowing Translation of Rotation", Journal of Arthroplasty 17 (2002): 11-19, 9 Pages.
European Patent Office, Search Report for App. No. 09164479.9-2310, mailed Nov. 4, 2009, 6 pages.
2nd Int'l Johnson-Elloy Knee Meeting, Mar. 1987, 9 pages.
Operative Technique, Johnson Elloy Knee System, Chas F. Thackray, Ltd., 1988, 34 pgs.
Operative Technique the Turning Point, Accord, The Johnson/Elloy Concept, Chas FL Thackray Ltd, 32 pages.
Restoration of Soft Tissue Stability, Johnson, et al., Chas. F. Thackray, Ltd., 21 pages.
The Accuracy of Intramedullary Alignment in Total Knee Replacement, Elloy, et al, Chas F. Thackray Ltd, 12 pages.
The Turning Point, Accord, The Johnson Elloy Concept, Chas F. Thackray Ltd, 20 pages.
Prosthesis and Instrumentation the Turning Point, Accord, The Johnson/Elloy Concept, Chas F. Thackray Ltd, 8 pages.
Five to Eight Year Results of the Johnson/Elloy (Accord) Total Knee Arthroplasty, Johnson et al, The Journal of Arthroplasty, vol. 8, No. 1, Feb. 1993, 6 pages.
Factors Affecting the Range of Movement of Total Knee Arthroplasty, Harvey et al, The Journal of Bone and Joint Surgery, vol. 75-B, No. 6, Nov. 1993, 6 pages.
Advice Notice (NI) 2000/03, Defect & Investigation Centre, Mar. 13, 2000, 3 pages.
The Johnson Elloy (Accord) Total Knee Replacement, Norton et al, The Journal of Bone and Joint Surgery (BR), vol. 84, No. 6, Aug. 2002, 4 pages.
Midvatus Approach in Total Knee Arthroplasty, A Description and a Cadaveric Study Determining the Distance of the Popliteal Artery From the Patellar Margin of the Incision, Cooper et al., The Journal of Arthoplasty, vol. 14 No. 4, 1999, 4 Pages.
European Search Report for European Patent Application No. 08164944.4-2310-2042131, Mar. 16, 2009, 12 pgs.
European Search Report for European Patent Application No. 09164160.5-1526, Jan. 4, 2010, 4 pgs.
European Search Report for European Patent Application No. 09164228.0-1526, Feb. 2, 2010, 6 pgs.

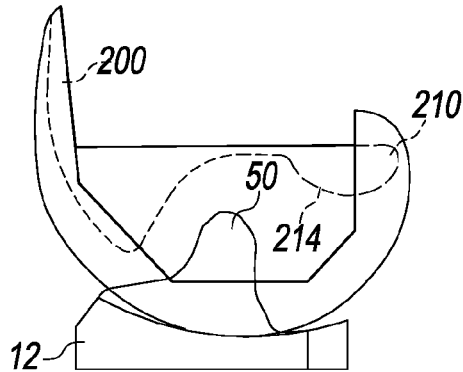
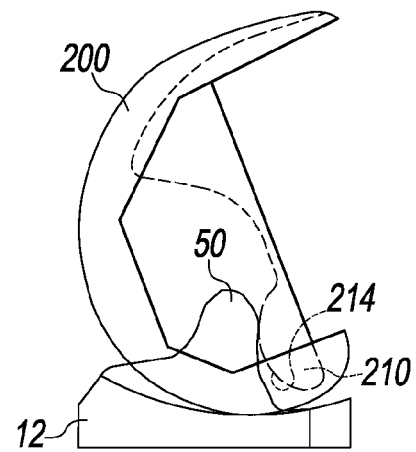
Fig. 11    Fig. 12
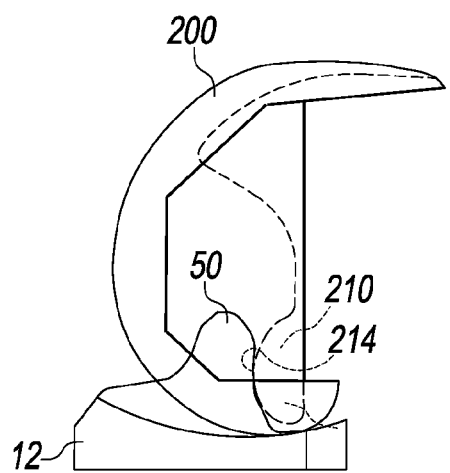
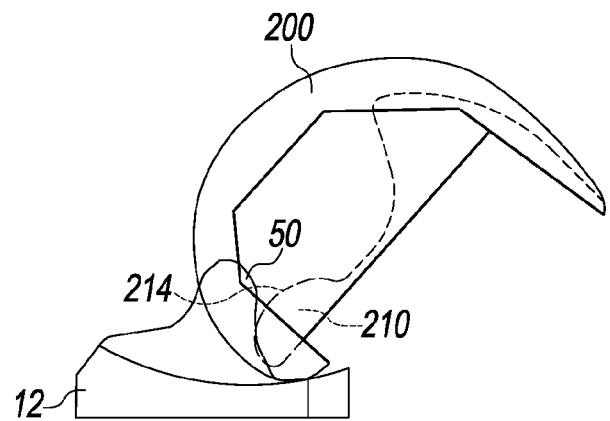
Fig. 13    Fig. 14

# POSTERIOR STABILIZED ORTHOPAEDIC PROSTHESIS ASSEMBLY

This application claims priority under 35 U.S.C. §120 to Utility Patent Application Ser. No. 61/503,348 entitled Posterior Stabilized Orthopaedic Prosthesis Assembly," which was filed on Jun. 30, 2011, the entirety of each of which is incorporated herein by reference. This application is a continuation-in-part application of Utility patent application Ser. No. 13/527,758 entitled "Posterior Stabilized Orthopaedic Prosthesis" by Joseph G. Wyss, which was filed on Jun. 20, 2012, the entirety of each of which is incorporated herein by reference.

TECHNICAL FIELD

The present disclosure relates generally to orthopaedic prostheses, and particularly to posterior stabilized orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. A knee prosthesis is generally designed to duplicate the natural movement of the patient's joint. However, depending on the severity of the damage to the patient's joint, orthopaedic prostheses of varying mobility may be used. For example, in some patients, the posterior cruciate ligament may be damaged, deficient, or removed during the orthopaedic surgical procedure. In such cases, a posterior stabilized knee orthopaedic prosthesis, which typically restricts or limits the posterior movement of the tibia relative to the femur, may be used.

SUMMARY

According to one aspect, an orthopaedic prosthesis assembly includes a tibial bearing, a first femoral component, and a second femoral component. The tibial bearing may be configured to be coupled to a tibial tray. The tibial bearing may include a platform and a spine extending upwardly from the platform. The spine may have a posterior cam surface that includes a concave cam surface and a convex cam.

Each of the first and second femoral components may be configured to separately couple with the tibial bearing to articulate with the tibial bearing. Additionally, each of the first and second femoral components may include a pair of spaced apart condyles defining an intracondylar notch therebetween and a posterior cam positioned in the intracondylar notch. Each posterior cam may include a posterior cam surface. The posterior cam surface of the first femoral component may include a concave cam surface and a convex cam surface. The concave cam surface of the posterior cam may contact the convex cam surface of the spine during a first range of flexion and the convex cam surface of the posterior cam may be configured to contact the concave cam surface of the spine during a second range of flexion. The posterior cam surface of the second femoral component may also be convex. In some embodiments, the first femoral component may be embodied as a primary femoral component and the second femoral component may be embodied as a secondary femoral component.

In some embodiments, the concave cam surface of the posterior cam surface of the first femoral component is concavely curved in the sagittal plane and the convex cam surface the posterior cam surface of the first femoral component is convexly curved in the sagittal plane. Additionally or alternatively, the concave cam surface and the convex cam surface of the posterior cam surface of the first femoral component may be concavely curved in the medial-lateral direction. In some embodiments, the posterior cam surface of the second femoral component is concavely curved in the medial-lateral direction. Additionally, in some embodiments, the posterior cam surfaces of the first and second femoral components are each concavely curved in the medial-lateral direction.

Additionally, in some embodiments, the convex cam surface of the spine of the tibial bearing may be convexly curved in the sagittal plane and the concave cam surface of the spine is concavely curved in the sagittal plane. Additionally or alternatively, the concave cam surface and the convex cam surface of the spine may be convexly curved in the transverse plane. In such embodiments, the radius of curvature in the transverse plane of the concave cam surface of the spine may be substantially equal to the radius of curvature in the transverse plane of the convex cam surface of the spine. In some embodiments, the convex cam surface of the spine of the tibial bearing may be located superiorly relative to the concave cam surface of the spine.

In some embodiments, the degrees of flexion of the first range of flexion may be less than the degrees of flexion of the second range of flexion. Additionally, in some embodiments, the concave cam surface of the spine of the tibial bearing may be defined by a first radius of curvature and the convex cam surface of the spine may be defined by a second radius of curvature that is different from the first radius of curvature. Additionally or alternatively, concave cam surface of the posterior cam surface of the first femoral component may be defined by a third radius of curvature and the convex cam surface of the posterior cam surface of the first femoral component may be defined by a fourth radius of curvature, the third radius of curvature being different from the fourth radius of curvature.

According to another aspect, an orthopaedic prosthesis assembly may include a tibial bearing, a primary femoral component and a revision femoral component. The tibial bearing may include a platform and a spine extending upwardly from the platform. The spine may include a posterior cam surface having a substantially "S"-shaped cross-section in the sagittal plane.

The primary femoral component may be configured to be coupled to a surgically-prepared distal end of a femur and include a posterior cam having a posterior cam surface. The posterior cam surface may have a substantially "S"-shaped cross-section in the sagittal plane. The revision femoral component may be configured to be coupled to the surgically-prepared distal end of the femur and include a posterior cam having a posterior cam surface that is convexly curved in the sagittal plane. Each of the primary and revision femoral components may be configured to couple to the tibial bearing and articulate with the tibial bearing such that the posterior cam surface of the respective primary and revision femoral component articulates on the posterior cam surface of the spine of the tibial bearing during a range of flexion.

In some embodiments, the posterior cam surfaces of the primary and the revision femoral components are each concavely curved in the transverse plane. Additionally, the posterior cam surface of the tibial bearing may include a concave cam surface and a convex cam surface in the sagittal plane. The concave cam surface may be concavely curved in the sagittal plane and the convex cam surface may be convexly curved in the sagittal plane. Additionally, in some embodiments, the concave cam surface and the convex cam surface of the posterior cam surface of the tibial bearing are curved in the transverse plane.

In some embodiments, the posterior cam surface of posterior cam of the primary femoral component may include a concave cam surface and a convex cam surface. The concave cam surface may be concavely curved in the sagittal plane and the convex cam surface may be convexly curved in the sagittal plane. Additionally, in some embodiments, each of the posterior cams of the primary and the revision femoral components may be configured to rotate about the spine of the tibial bearing in the transverse plane when the respective primary and revision femoral component articulates with the tibial bearing.

According to a further aspect, a posterior stabilized knee orthopaedic prosthesis assembly may include a tibial bearing, a primary femoral component, and a revision femoral component. Each of the primary and revision femoral components may be configured to separately couple with the tibial bearing and articulate on the tibial bearing during a range of flexion. The tibial bearing may include a platform having a medial bearing surface and a lateral bearing surface and a spine extending upwardly from the platform between the medial bearing surface and the lateral bearing surface. The spine may include a posterior side having a superior cam surface and an inferior cam surface. The superior cam surface may be convexly curved in the sagittal plane and the inferior cam surface may be concavely curved in the sagittal plane. The superior cam surface and the inferior cam surface may be convexly curved in the transverse plane.

The primary femoral component may include a primary lateral condyle configured to articulate with the lateral bearing surface of the tibial bearing, a primary medial condyle configured to articulate with the medial bearing surface, and a primary posterior cam positioned in a primary intracondylar notch defined between the primary lateral condyle and the primary medial condyle. The primary posterior cam may include a primary concave cam surface and a primary convex cam surface. The primary concave posterior cam surface may be positioned to initially contact the superior cam surface of the spine at a first degree of flexion. Additionally, the primary convex cam surface may be positioned to initially contact the inferior cam surface of the spine at a second degree of flexion greater than the first degree of flexion.

The revision femoral component may include a revision lateral condyle configured to articulate with the lateral bearing surface of the tibial bearing, a revision medial condyle configured to articulate with the medial bearing surface, and a revision posterior cam positioned in a revision intracondylar notch defined between the revision lateral condyle and the revision medial condyle. The revision posterior cam may include a revision convex cam surface that is positioned to initially contact the superior cam surface of the spine at a third degree of flexion and initially contact the inferior cam surface of the spine at a fourth degree of flexion greater than the third degree of flexion.

BRIEF DESCRIPTION OF THE DRAWINGS

The detailed description particularly refers to the following figures, in which:

FIGS. 11-14 are side elevational views of the orthopaedic prosthesis of FIG. 1 using the revision femoral component of FIG. 6 at various degrees of flexion.

DETAILED DESCRIPTION OF THE DRAWINGS

Figure 1:
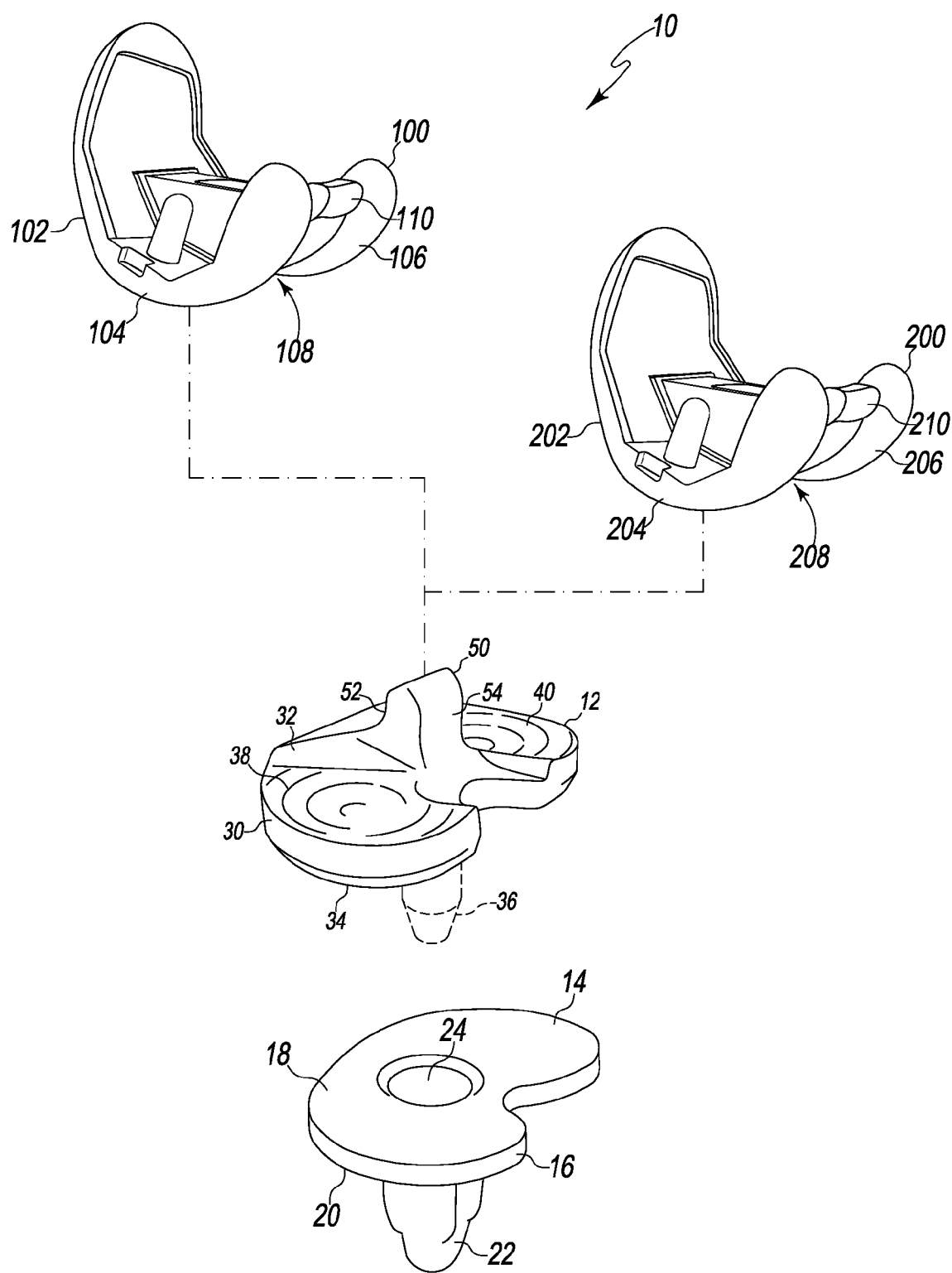
FIG. 1 is an exploded perspective view of one embodiment of an orthopaedic prosthesis assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior stabilized knee orthopaedic prosthesis assembly 10 includes a tibial insert or bearing 12, a tibial tray 14, a primary femoral component 100, and a revision femoral component 200. The primary and revision femoral components 100, 200 are each configured to separately couple to and articulate with the tibial bearing 12 during use. That is, based on the particular orthopaedic surgery to be performed, the preference of the orthopaedic surgeon, and/or other factors, the surgeon may select one of the femoral components 100, 200 to use with the tibial bearing 12 in the orthopaedic surgical procedure. Typically, the primary femoral component 100 is used for the initial orthopaedic surgical procedure on the patient (e.g., the first total knee arthroplasty procedure performed on a patient's particular knee), and the revision femoral component 200 is sued for subsequent orthopaedic surgical procedures (e.g., procedures to correct misalignment, loosening of components, etc.). Of course, an orthopaedic surgeon may use either femoral components 100, 200 during any particular orthopaedic surgery. It should be appreciated, however, that because each of the primary femoral component 100, and the revision femoral component 200 is configured to be used with the same tibial bearing 12, the overall number of components of a typical primary/revision orthopaedic prosthesis assembly is reduced because a single tibial bearing 12 is used with either femoral components 100, 200.

The tibial bearing 12 is illustratively formed from a polymer material such as a ultra-high molecular weight polyethylene (UHMWPE), but may be formed from other materials, such as a ceramic material, a metallic material, a bio-engineered material, or the like, in other embodiments. The illustrative tibial bearing 12 is embodied as a rotating or mobile tibial bearing and is configured to rotate relative to the tibial tray 14 during use. However, in other embodiments, the tibial bearing 12 may be embodied as a fixed tibial bearing, which may be limited or restricted from rotating relative the tibial tray 14.

The tibial tray 14 is configured to be secured to a surgically-prepared proximal end of a patient's tibia (not shown). The tibial tray 14 may be secured to the patient's tibia via use of bone adhesive or other attachment means. The tibial tray 14 includes a platform 16 having a top surface 18 and a bottom surface 20. Illustratively, the top surface 18 is generally planar and, in some embodiments, may be highly polished. The tibial tray 14 also includes a stem 22 extending downwardly from the bottom surface 20 of the platform 16. A cavity or bore 24 is defined in the top surface 18 of the platform 16 and extends downwardly into the stem 22. The bore 24 is formed to receive a complimentary stem of the tibial bearing 12 as discussed in more detail below.

As discussed above, the tibial bearing 12 is configured to be coupled with the tibial tray 14. The tibial bearing 12 includes a platform 30 having an upper bearing surface 32 and a bottom surface 34. In the illustrative embodiment wherein the tibial bearing 12 is embodied as a rotating or mobile tibial bearing, the bearing 12 includes a stem 36 extending downwardly from the bottom surface 34 of the platform 30. When the tibial bearing 12 is coupled to the tibial tray 14, the stem 36 is received in the bore 24 of the tibial tray 14. In use, the tibial bearing 12 is configured to rotate about an axis defined by the stem 36 relative to the tibial tray 14. In embodiments wherein the tibial bearing 12 is embodied as a fixed tibial bearing, the bearing 12 may or may not include the stem 36 and/or may include other devices or features to secure the tibial bearing 12 to the tibial tray 14 in a non-rotating configuration.

The upper bearing surface 32 of the tibial bearing 12 includes a medial bearing surface 38, a lateral bearing surface 40, and a spine 50 extending upwardly from the platform 30. The medial and lateral bearing surfaces 38, 40 are configured to receive or otherwise contact corresponding medial and lateral condyles of one of the femoral components 100, 200 as discussed in more detail below. As such, the bearing surfaces 38, 40 may have concave contours in some embodiments. The spine 50 is positioned between the bearing surfaces 38, 40 and includes an anterior side 52 and a posterior side 54.

Each of the primary femoral component 100 and the revision femoral component 200 is illustratively formed from a metallic material such as cobalt-chromium or titanium, but may be formed from other materials, such as a ceramic material, a polymer material, a bio-engineered material, or the like, in other embodiments. As discussed above, each of the femoral components 100, 200 is configured to articulate with the tibial bearing 12 and has similar geometry to each other.

The primary femoral component 100 is configured to be coupled to a surgically-prepared surface of the distal end of a patient's femur (not shown). The femoral component 100 may be secured to the patient's femur via use of bone adhesive or other attachment means. The femoral component 100 includes an articulating surface 102 having a pair of spaced apart medial and lateral condyles 104, 106. In use, the condyles 104, 106 replace the natural condyles of the patient's femur and are configured to articulate on the corresponding bearing surfaces 38, 40 of the platform 30 of the tibial bearing 12.

The condyles 104, 106 are spaced apart to define an intracondyle notch or recess 108 therebetween. A posterior cam 110 and an anterior cam 112 (see FIG. 4) are positioned in the intracondyle notch 108. The posterior cam 110 is located toward the posterior side of the femoral component 100 and is configured to engage or otherwise contact the spine 50 of the tibial bearing 12 during flexion as described in more detail below.

The revision femoral component 200 is similar to the primary femoral component 100 and is also configured to be coupled to a surgically-prepared surface of the distal end of a patient's femur (not shown) in lieu of the primary femoral component 100. As with the primary femoral component 100, the femoral component 200 may be secured to the patient's femur via use of bone adhesive or other attachment means. The femoral component 200 includes an articulating surface 202 having a pair of spaced apart medial and lateral condyles 204, 206. In use, the condyles 204, 206 replace the natural condyles of the patient's femur and are configured to articulate on the corresponding bearing surfaces 38, 40 of the platform 30 of the tibial bearing 12.

The condyles 204, 206 are spaced apart to define an intracondyle notch or recess 208 therebetween. A posterior cam 210 and an anterior cam 212 (see FIG. 6) are positioned in the intracondyle notch 208. The posterior cam 210 is located toward the posterior side of the femoral component 200 and is configured to engage or otherwise contact the spine 50 of the tibial bearing 12 during flexion as described in more detail below.

Figure 2:
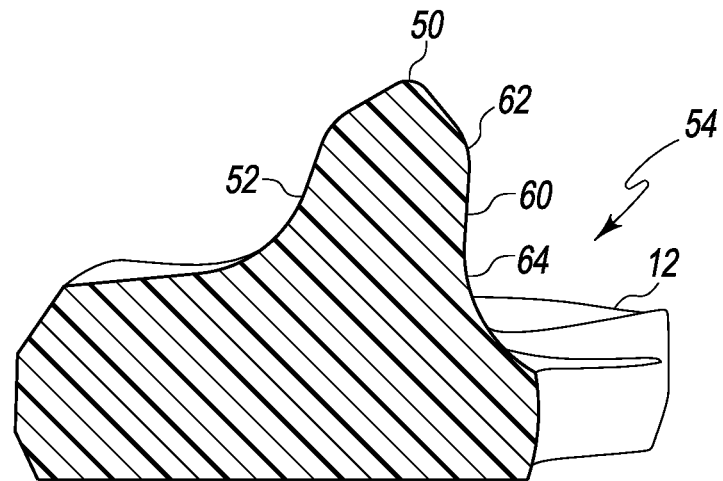
FIG. 2 is a cross-sectional view of one embodiment of a tibial bearing of the orthopaedic prosthesis assembly of FIG. 1.
Figure 3:
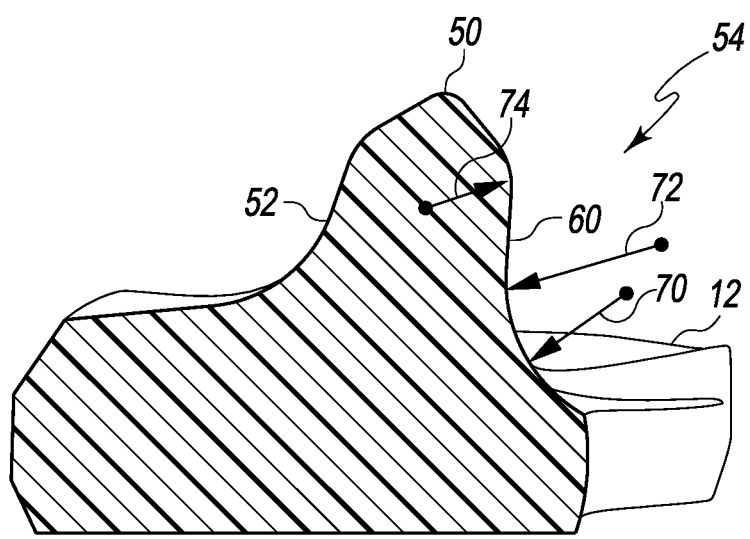
FIG. 3 is a cross-sectional view of another embodiment of a tibial bearing of the orthopaedic prosthesis assembly of FIG. 1.

Referring now to FIGS. 2 and 3, the spine 50 of the tibial bearing 12 includes a cam surface 60 on the posterior side 54 of the spine 50. The cam surface 60 is configured to contact and articulate with the posterior cams 110, 210 of the femoral components 100, 200 during use. Illustratively, the cam surface 60 of the spine 50 has a substantially "S"-shaped cross-sectional profile in the sagittal plane. In particular, the cam surface 60 includes a convex cam surface 62 and a concave cam surface 64. In the illustrative embodiment, the convex cam surface 62 is positioned superiorly relative to the concave cam surface 64. The cam surfaces 62, 64 of the spine 50 may have similar or different radius of curvatures. For example, in some embodiments, the concave cam surface 64 has a radius of curvature substantially larger than the radius of curvature of the convex cam surface 62. However, in other embodiments, the concave cam surface 64 may have a radius of curvature that is substantially equal to or less than the radius of curvature of the convex cam surface 62.

In some embodiments, the curvature of the cam surfaces 62, 64 may be defined by a single radius of curvature. The particular radius of curvature of the cam surfaces 62, 64 (i.e., the "size" of the cam surfaces) may be dependent upon a number of criteria such as the size of the implant, the shape or geometry of the articulating surface of the posterior cams 110, 210 of the femoral components 100, 200, and/or the like. In other embodiments, however, the convex cam surface 62 and the concave cam surface 64 of the tibial bearing 12 may be formed from multiple radii of curvature. For example, in the embodiment illustrated in FIG. 3, the concave cam surface 64 is defined by a radius of curvature 70 and a radius of curvature 72, each of which is tangent to the other. In one particular embodiment, the radius of curvature 70 is about 9.00 millimeters and the radius of curvature 72 is about 13.00 millimeters. The convex cam surface 62 is defined by a radius of curvature 74. In one particular embodiment, the radius of curvature 74 is about 8.00 millimeters. Of course, in other embodiments, a larger or lesser number of radii of curvature may be used define the cam surfaces 62, 64. Additionally, the radii of curvature 70, 72, 74 may have other values in other embodiments.

Figure 4:
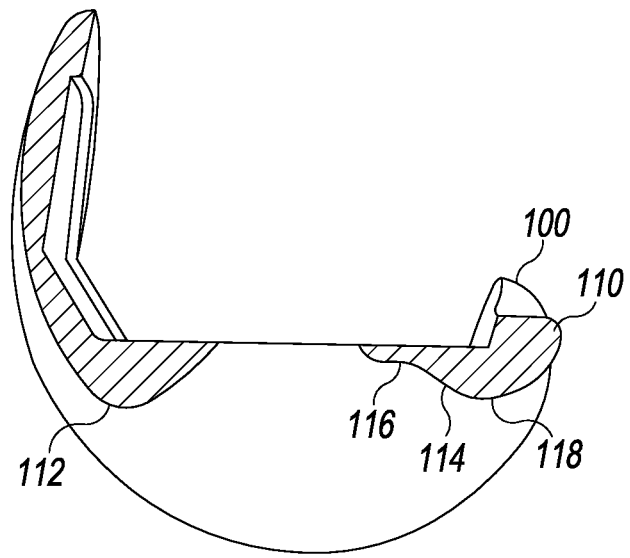
FIG. 4 is a cross-sectional view of one embodiment of a primary femoral component of the orthopaedic prosthesis assembly of FIG. 1.
Figure 5:
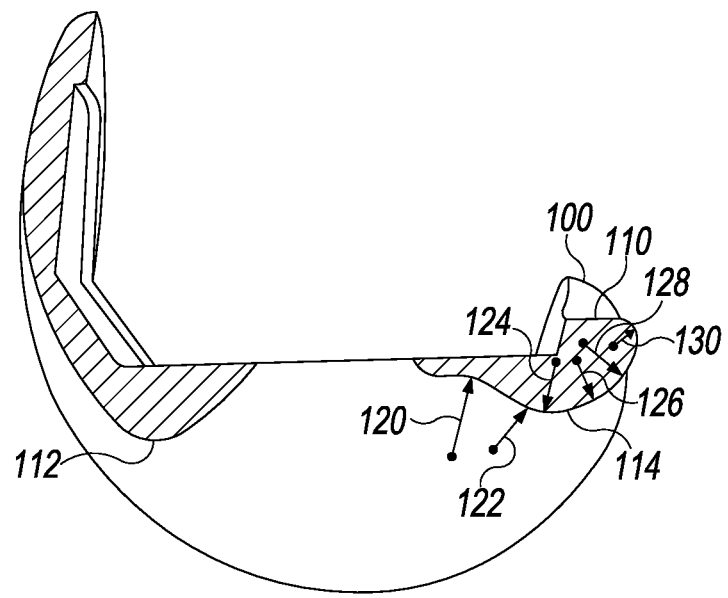
FIG. 5 is a cross-sectional view of another embodiment of a primary femoral component of the orthopaedic prosthesis assembly of FIG. 1.

Referring now to FIGS. 4 and 5, the posterior cam 110 of the primary femoral component 100 includes a cam surface 114 configured to contact the cam surface 60 of the spine 50 during use. Similar to the cam surface 60 of the spine 50, the cam surface 114 of the posterior cam 110 has a substantially "S"-shaped cross-sectional profile in the sagittal plane. In particular, the cam surface 114 includes a concave cam surface 116 and a convex cam surface 118. In the illustrative embodiment, the convex cam surface 118 is positioned posteriorly to the concave cam surface 116. The cam surfaces 116, 118 may have similar or different radius of curvatures. For example, in some embodiments, the convex cam surface 118 may have a radius of curvature substantially larger than the radius of curvature of the concave cam surface 116. However, in other embodiments, the convex cam surface 118 may have a radius of curvature that is substantially equal to or less than the radius of curvature of the concave cam surface 116.

In some embodiments, the curvature of the cam surfaces 116, 118 may be defined by a single radius of curvature. The particular radius of curvature of the cam surfaces 116, 118 (i.e., the "size" of the cam surfaces) may be dependent upon a number of criteria such as the size of the implant, the shape or geometry of the cam surface 60 of the spine 50 of the tibial bearing 12, and/or the like. In other embodiments, however, the concave cam surface 116 and the convex cam surface 118 of the femoral component 100 may be formed from multiple radii of curvature. For example, in the embodiment illustrated in FIG. 5, the concave cam surface 116 is defined by a radius of curvature 120 and a radius of curvature 122, each of which is tangent to the other. In one particular embodiment, the radius of curvature 120 is about 10.42 millimeters and the radius of curvature 122 is about 8.13 millimeters. Additionally, the convex cam surface 118 is defined by a plurality of radii of curvature 124, 126, 128, and 130. Each of the radii of curvature 124, 126, 128, 130 is tangent with the each adjacent radius of curvature. In one particular embodiment, the radius of curvature 124 is about 7.14 millimeters, the radius of curvature 126 is about 7.01 millimeters, the radius of curvature 128 is about 7.30 millimeters, and the radius of curvature 130 is about 2.30 millimeters. In other embodiments, a larger or lesser number of radii of curvature may be used define the cam surfaces 116, 118. Additionally, the radii of curvature 124, 126, 128, 130 may have other values in other embodiments.

Figure 6:
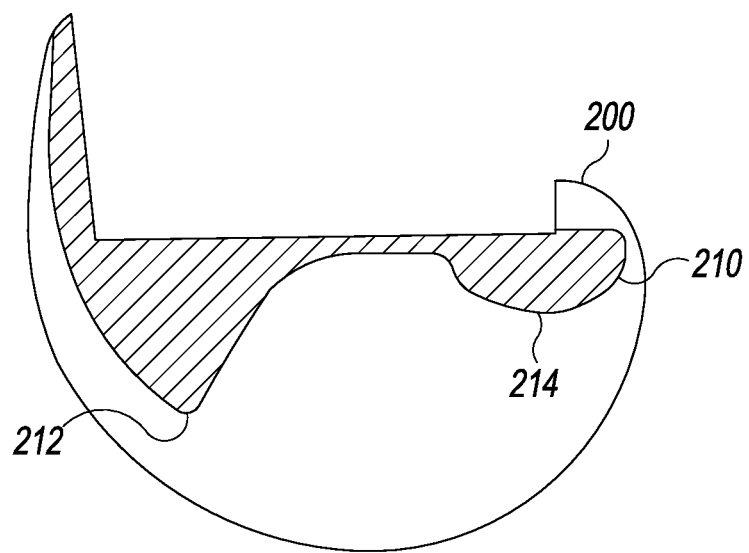
FIG. 6 is a cross-sectional view of one embodiment of a revision femoral component of the orthopaedic prosthesis assembly of FIG. 1.

Referring now to FIG. 6, similar to the posterior cam 110 of the primary femoral component 100, the posterior cam 210 of the revision femoral component 200 includes a cam surface 214 configured to contact the cam surface 60 of the spine 50 during use. However, unlike the posterior cam 110 of the primary femoral component 100, the cam surface 214 does not have a substantially "S"-shaped cross-sectional profile in the sagittal plane. Rather, the cam surface 214 is embodied as a substantially cam surface. In the illustratively embodiment, the cam surface 214 is uniformly convex. That is, the illustrative cam surface 214 does not include a concave section. In one embodiment, the convex cam surface 214 is defined by a single radius of curvature. However, in other embodiments, the convex cam surface 214 may be defined by multiple radii of curvature, each having a different length so as to define a convex cam surface having multiple convex curved surface sections that cooperate to define the convex cam surface 214.

In use, an orthopaedic surgeon may use either the primary femoral component or the revision femoral component depending on the patient's anatomy, the type of orthopaedic surgical procedure being performed, the surgeon's preference, and/or other criteria. As discussed above, each of the femoral components 100, 200 are configured to articulate with the tibial bearing 12. During flexion, the posterior cams 110, 210 of the femoral components 100, 200 are configured to contact the spine 50 of the tibial bearing 12.

Figure 7:
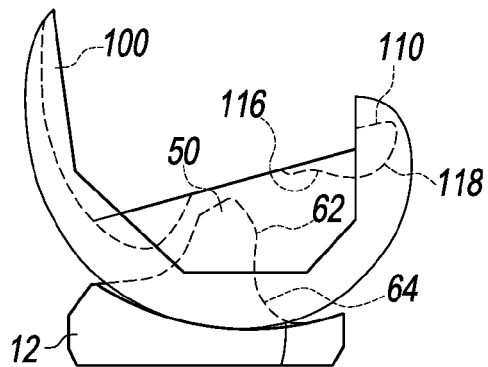
FIGS. 7-10 are side elevational views of the orthopaedic prosthesis of FIG. 1 using the primary femoral component of FIG. 4 at various degrees of flexion.
Figure 8:
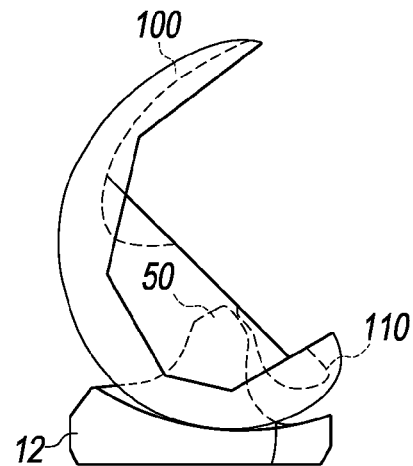

In embodiments wherein the primary femoral component 100 is used, the concave cam surface 116 of the posterior cam 110 contacts the convex cam surface 62 of the spine 50 during early flexion. As flexion of the femoral component 100 and tibial bearing 12 is increased, the contact between the posterior cam 110 and the spine 50 transitions from contact between the concave cam surface 116 of the posterior cam 110 and the convex cam surface 62 of the spine 50 to contact between the convex cam surface 118 of the posterior cam 110 and the concave cam surface 64 of the spine 50 during late flexion. For example, as shown in FIG. 7, when the femoral component 100 and tibial bearing 12 are in extension or are otherwise not in flexion (e.g., a flexion of about 0 degrees), the posterior cam 110 is not in contact with the spine 50. However, during early flexion as illustrated in FIG. 8, the posterior cam 110 of the femoral component 100 contacts the spine 50 of the tibial bearing 12. As the femoral component 100 and tibial bearing 12 are moved in flexion, the concave cam surface 116 of the posterior cam 110 initially contacts the convex cam surface 62 of the spine 50 at a predetermined degree of flexion and maintains contact through early flexion. In the illustrative embodiment, the femoral component 100 and the tibial bearing 12 are configured such that the cam surfaces 116, 62 initially contact each other at about 60 degrees of flexion. However, in other embodiments, the degree of flexion at which initial contact between the posterior cam 110 and the spine 50 is established may be determined based on particular criteria such as the size of the orthopaedic prosthesis 10, the shape or geometry of the articulating surface of the primary femoral component 100 and/or the tibial bearing 12, and/or the like.

Figure 9:
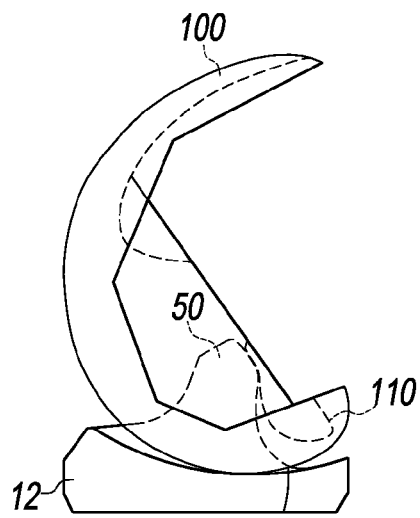
Figure 10:
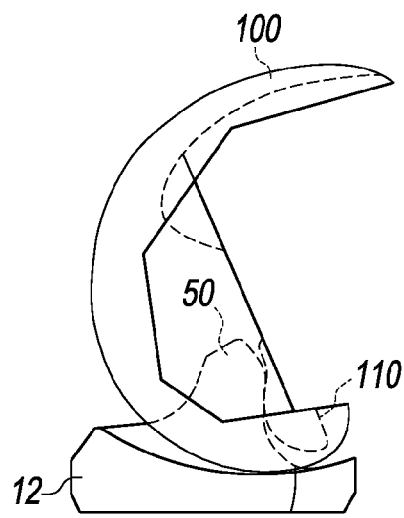

After early flexion, the contact between the posterior cam 110 and the spine 50 transitions from the cam surfaces 116, 62 to the cam surfaces 118, 64. For example, as illustrated in FIG. 9, the contact between the posterior cam 110 and the spine 50 begins transitioning to the cam surfaces 118, 64 at about 80 degrees. At this degree of flexion, initial contact between the convex cam surface 118 of the posterior cam 110 and the concave cam surface 64 of the spine 50 may be established. During late flexion of the femoral component 100 and tibial bearing 12, the convex cam surface 118 maintains contact with the concave cam surface 64 as shown in FIG. 10.

It should be appreciated that contact between the posterior cam 110 and the spine 50 is maintained throughout the range of early and late flexion. The particular range of early flexion (i.e., the range at which the concave cam surface 116 of the posterior cam 110 contacts the convex cam surface 62 of the spine 50) and late flexion (i.e., the range at which the convex cam surface 118 of the posterior cam 110 contacts the concave cam surface 64 of the spine 50) of the femoral component 100 and the tibial bearing 12 may be dependent upon one or more criteria such as the size of the primary femoral component 100 and the tibial bearing 12, the shape or geometry of the articulating cam surfaces of the tibial bearing 12 and the primary femoral component 100, or the like. In the illustrative embodiment, the primary femoral component 100 and the tibial bearing 12 are configured to have an early flexion range of about 50 degrees to about 80 degrees and a late flexion range of about 80 degrees to about 150 degrees, but other ranges of flexion may be used in other embodiments. The range of early and late flexion is determined, in part, based on the radius of curvature of the cam surfaces 116, 118, 62, 64. As such, the range of early and late flexion of the interaction between the primary femoral component 100 and the tibial bearing 12 may be configured by adjusting the radius of curvature of the cam surfaces 116, 118, 62, 64.

It should also be appreciated that because the cam surface 114 of the posterior cam 110 includes the concave cam surface 116 and the convex cam surface 118 and the cam surface 54 of the spine 50 includes the convex cam surface 62 and the concave cam surface 64, the contact surface area between the posterior cam 110 of the primary femoral component 100 and the spine 50 is increased through the flexion range relative to orthopaedic prostheses wherein the posterior cam and/or the spine include planar cam surfaces or cam surfaces having only a concave or convex surface. For example, the contact area between the posterior cam 110 and the spine 50 is increased in early flexion due to the interface between the concave cam surface 116 of the posterior cam 110 and the convex cam surface 62 of the spine 50. Additionally, in late flexion, the contact area between the posterior cam 110 and the spine 50 is increased in later degrees of flexion due to the interface between the convex cam surface 118 of the posterior cam 110 and the concave cam surface 64 of the spine 50.

Referring now to FIGS. 11-14, in embodiments wherein the revision femoral component 200 is used, the cam surface 214 of the posterior cam 210 contacts the convex cam surface 62 of the spine 50 of the tibial bearing 12 during early flexion. As discussed above, the cam surface 214 of the femoral component 200 is substantially uniformly convex in the sagittal plane relative to the cam surface 114 of the femoral component 200, which includes the concave cam surface 116 and the convex cam surface 118. As flexion of the femoral component 200 on the tibial bearing 12 is increased, the contact between the posterior cam 210 and the spine 50 transitions from contact between the convex cam surface 214 of the posterior cam 210 and the convex cam surface 62 of the spine 50 to contact between the convex cam surface 214 of the posterior cam 210 and the concave cam surface 64 of the spine 50 during late flexion. For example, as shown in FIG. 11, when the femoral component 200 and tibial bearing 12 are in extension or are otherwise not in flexion (e.g., a flexion of about 0 degrees), the posterior cam 210 is not in contact with the spine 50. However, during early flexion as illustrated in FIG. 12, the posterior cam 210 of the femoral component 200 contacts the spine 50 of the tibial bearing 12. As the femoral component 200 and tibial bearing 12 are moved in flexion, the posterior cam 210 initially contacts the convex cam surface 62 of the spine 50 at a predetermined degree of flexion and maintains contact through early flexion. In the illustrative embodiment, the revision femoral component 200 and the tibial bearing 12 are configured such that the cam surfaces 214, 62 initially contact each other at about 60 degrees of flexion. However, in other embodiments, the degree of flexion at which initial contact between the posterior cam 210 and the spine 50 is established may be determined based on particular criteria such as the size of the orthopaedic prosthesis 10, the shape or geometry of the articulating surface of the revision femoral component 200 and/or the tibial bearing 12, and/or the like.

After early flexion, the contact between the posterior cam 210 and the spine 50 transitions from the cam surfaces 210, 62 to the cam surfaces 214, 64. For example, as illustrated in FIG. 13, the contact between the posterior cam 210 and the spine 50 begins transitioning to the cam surfaces 214, 64 at about 80 degrees. At this degree of flexion, initial contact between the convex cam surface 214 of the posterior cam 210 and the concave cam surface 64 of the spine 50 may be established. During late flexion of the revision femoral component 200 and the tibial bearing 12, the convex cam surface 214 maintains contact with the concave cam surface 64 of the spine 50 as shown in FIG. 14

As with the posterior cam 110, it should be appreciated that contact between the posterior cam 210 and the spine 50 is maintained throughout the range of early and late flexion. The particular range of early flexion (i.e., the range at which the convex cam surface 214 of the posterior cam 210 contacts the convex cam surface 62 of the spine 50) and late flexion (i.e., the range at which the convex cam surface 214 of the posterior cam 210 contacts the concave cam surface 64 of the spine 50) of the revision femoral component 200 and the tibial bearing 12 may be dependent upon one or more criteria such as the size of the revision femoral component 200 and the tibial bearing 12, the shape or geometry of the articulating cam surfaces of the tibial bearing 12 and the revision femoral component 200, or the like. In the illustrative embodiment, the revision femoral component 200 and the tibial bearing 12 are configured to have an early flexion range of about 50 degrees to about 80 degrees and a late flexion range of about 80 degrees to about 150 degrees, but other ranges of flexion may be used in other embodiments. The range of early and late flexion is determined, in part, based on the radius of curvature of the cam surfaces 214, 62, 64. As such, the range of early and late flexion of the interaction between the revision femoral component 200 and the tibial bearing 12 may be configured by adjusting the radius of curvature of the cam surfaces 214, 62, 64.

Figure 15:
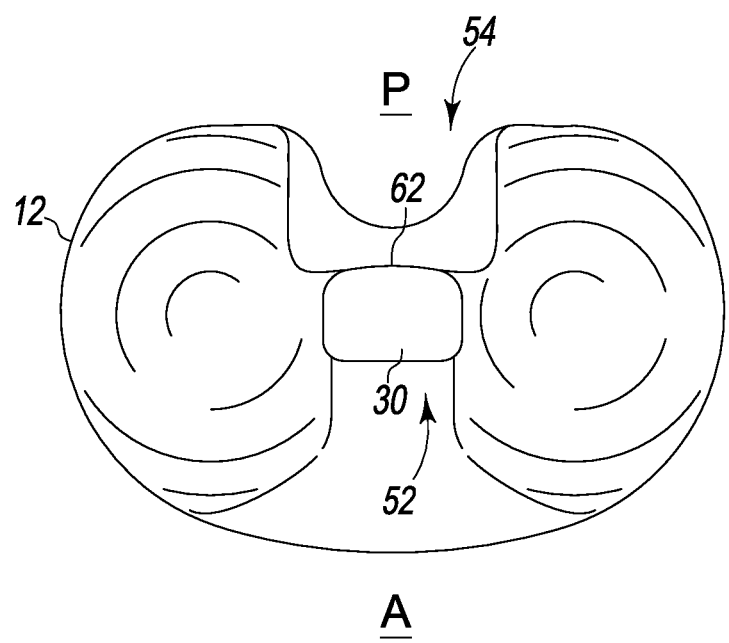
FIG. 15 is a top plan view of another embodiment of the tibial bearing of the orthopaedic prosthesis of FIG. 1.
Figure 16:
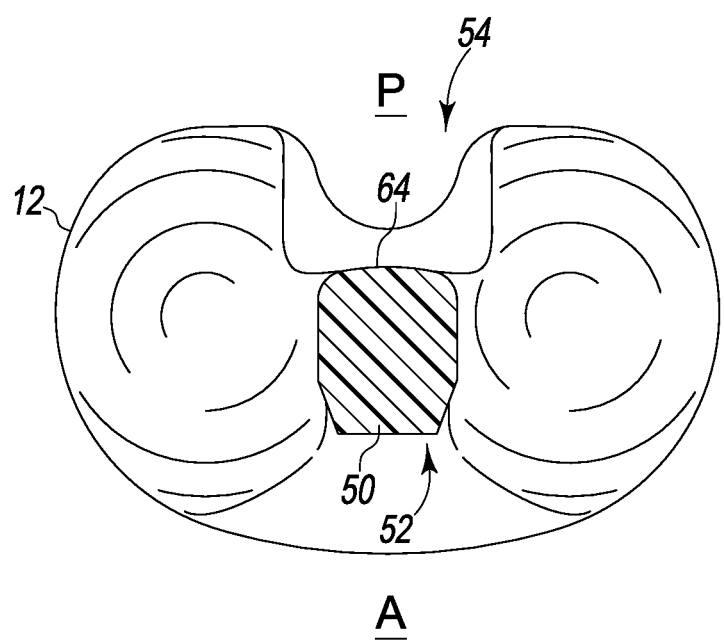
FIG. 16 is a cross-sectional plan view of the tibial bearing of FIG. 15 having a portion of the spine removed.
Figure 17:
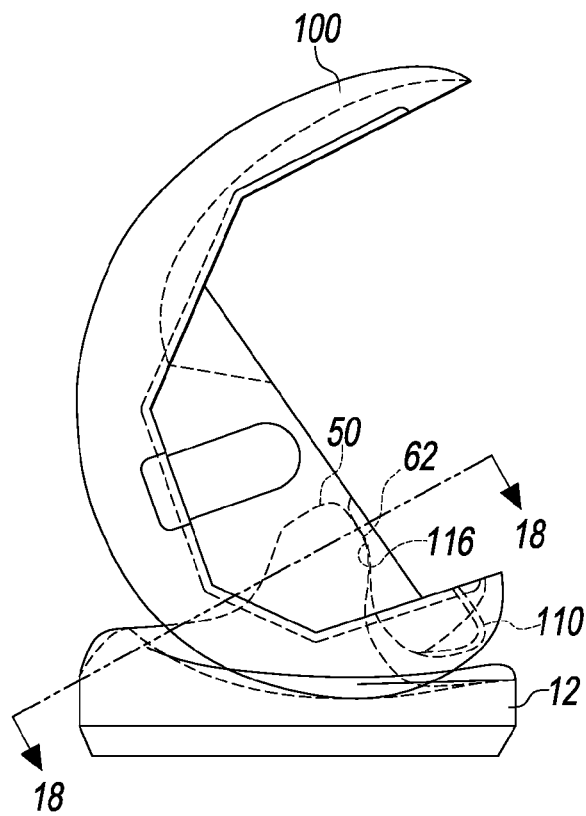
FIG. 17 is a side elevational view of one embodiment of the orthopaedic prosthesis assembly 10 using the primary femoral component of FIG. 4 and the tibial bearing of FIGS. 15 and 16 positioned in an early degree of flexion.

Referring now to FIGS. 15 and 17, in some embodiments, the posterior side 54 of the spine 50 may also be curved in the transverse plane. That is, each of the superior, convex cam surface 62 and the inferior, concave cam surface 64 may be convex in the transverse plane direction. For example, as illustrated in FIG. 15, the convex cam surface 62 of the spine 50 may be convexly curved in the transverse plane. Additionally, as illustrated in FIG. 16, the concave cam surface 64 of the spine 50 may be convexly curved in the transverse plane. The radius of curvature in the transverse plane of the convex cam surface 62 and the concave cam surface 64 may be substantially equal or different. For example, in some embodiments, the radius of curvature in the transverse plane of the concave cam surface 64 may be greater than the radius of curvature in the transverse plane of the convex cam surface 62. Alternatively, in other embodiments, the radius of curvature in the transverse plane of the convex cam surface 62 may be greater than the radius of curvature in the transverse plane of the concave cam surface 64.

Figure 18:
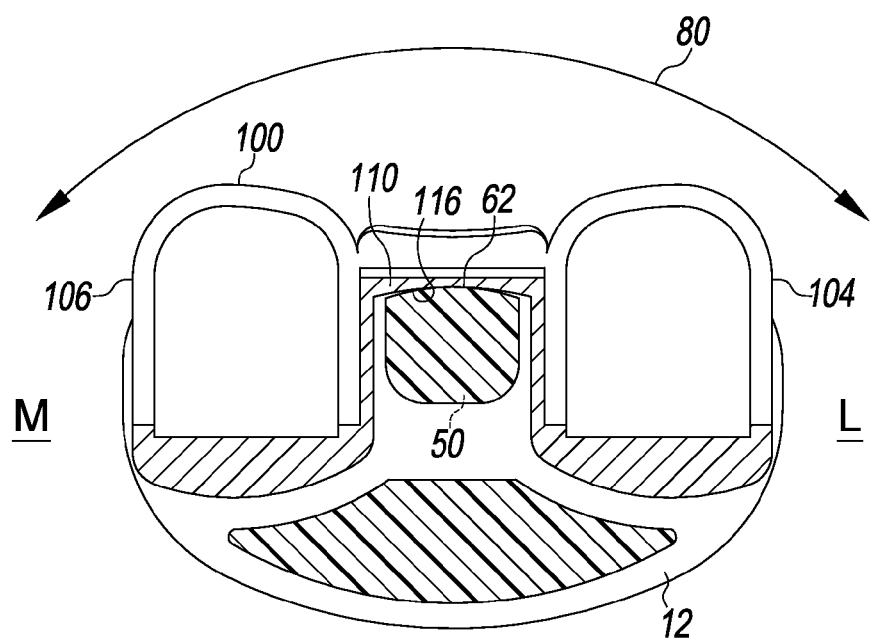
FIG. 18 is a cross-sectional view of the orthopaedic prosthesis assembly of FIG. 17 taken generally along the section line 18-18.

In embodiments wherein the cam surfaces 62, 64 of the spine 50 are curved in the transverse plane, the posterior cams 110, 210 of the femoral components 100, 200 articulate on the cam surfaces 62, 64 in the transverse plane such that the femoral components 100, 200 rotate an amount about the spine 50. An example of such rotation using the primary femoral component 100 and the tibial bearing 12 is illustrated in FIGS. 17-20. For example, as illustrated in FIGS. 17 and 18, when the concave cam surface 116 of the posterior cam 110 of the femoral component 100 is in contact with the convex cam surface 62 of the spine 50 during early flexion, the femoral component 100 may rotate about the spine 50 in a generally medial-lateral direction in the transverse plane as indicated by arrow 80. In such embodiments, the concave cam surface 116 of the posterior cam 110 may be substantially planar in the medial-lateral direction in some embodiments. Alternatively, similar to the convex cam surface 62 of the spine 50, the concave cam surface 116 of the posterior cam 110 of the femoral component 100 may also be curved in the medial-lateral direction. For example, as illustrated in FIG. 18, the concave cam surface 116 may be concavely curved in the medial-lateral direction. In some embodiments, the radius of curvature in the medial-lateral direction of the concave cam surface 116 may be substantially equal to the radius of curvature in the transverse plane of the convex cam surface 62 of the spine 50. Alternatively, the radius of curvature in the medial-lateral direction of the concave cam surface 116 may be greater or less than the radius of curvature in the transverse plane of the convex cam surface 62. The amount of rotation between the femoral component 100 and the tibial bearing 12 during early flexion may be adjusted based on the radius of curvatures in the transverse plane of the cam surfaces 116, 62. For example, an increased amount of rotation during early flexion of the orthopaedic prosthesis may be obtained by decreasing the radius of curvature in the transverse plane of the convex cam surface 62.

Figure 19:
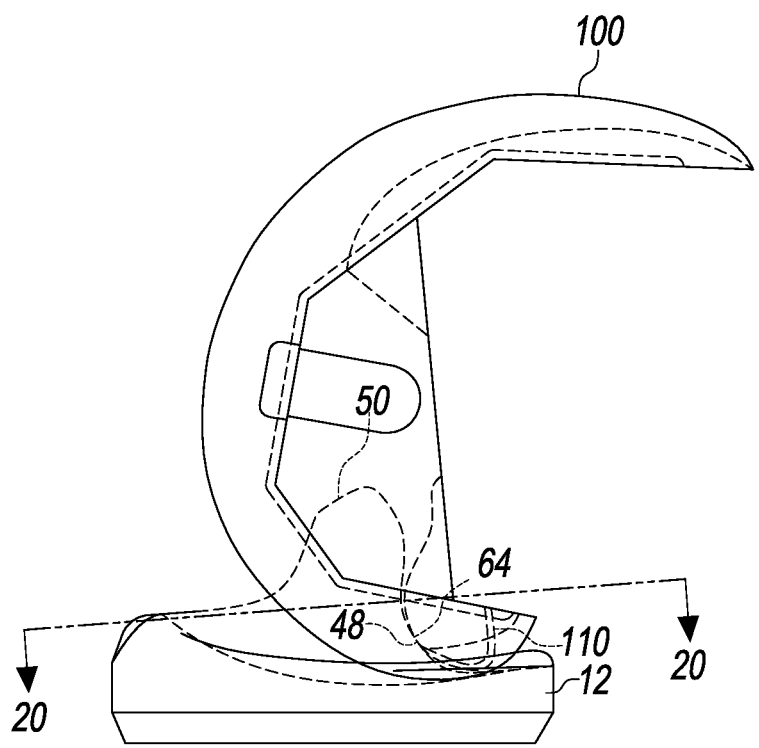
FIG. 19 is a side elevational view of one embodiment of the orthopaedic prosthesis assembly 10 of FIG. 17 positioned in a late degree of flexion.
Figure 20:
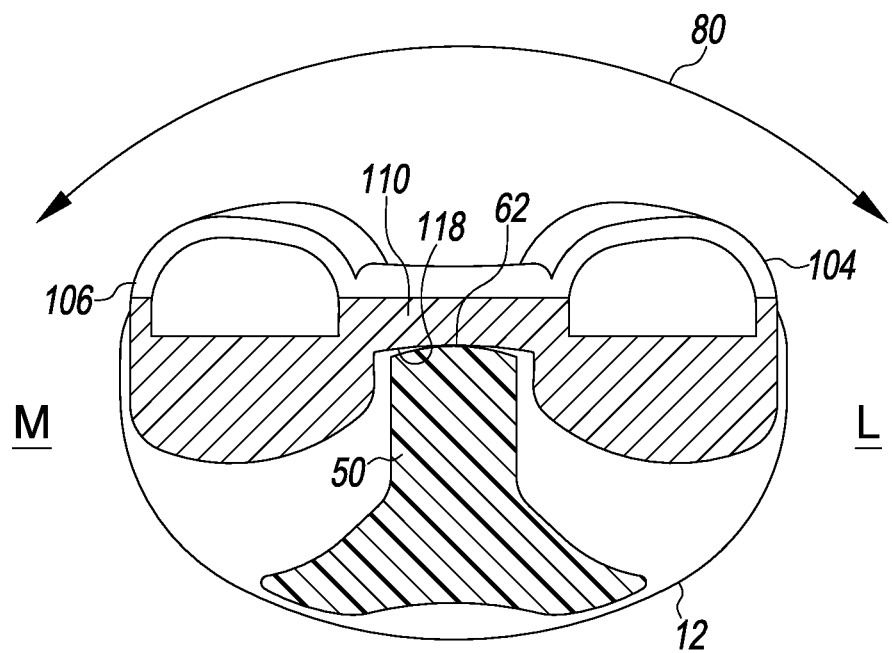
FIG. 20 is a cross-sectional view of the orthopaedic prosthesis of FIG. 7 taken generally along the section line 19-19.

Referring now to FIGS. 19 and 20, when the convex cam surface 118 of the posterior cam 110 is in contact with the concave cam surface 64 of the spine 50 during late flexion, the femoral component 100 may rotate about the spine 50 in a generally medially-laterally direction in the transverse plane as indicated by arrow 82 in some embodiments. In such embodiments, the convex cam surface 118 of the posterior cam 110 may be substantially planar in the medial-lateral direction. Alternatively, similar to the concave cam surface 64 of the spine 50, the convex cam surface 118 of the posterior cam 110 of the primary femoral component 100 may be curved in the medial-lateral direction. For example, as illustrated in FIG. 20, the convex cam surface 118 may be concavely curved in the medial-lateral direction. In some embodiments, the radius of curvature in the medial-lateral direction of the convex cam surface 118 may be substantially equal to the radius of curvature in the medial-lateral direction of the concave cam surface 64 of the spine 50. Alternatively, the radius of curvature in the medial-lateral direction of the convex cam surface 118 may be greater or slightly less than the radius of curvature in the medial-lateral direction of the concave cam surface 64. As discussed above in regard to early flexion, the amount of rotation between the primary femoral component 100 and the tibial bearing 12 during late flexion may be adjusted based on the radius of curvatures in the medial-lateral direction of the cam surfaces 118, 64.

It should be appreciated that the posterior cam 210 of the revision femoral component 200 may be substantially planar in the medial-lateral direction in some embodiments. Alternatively, the posterior cam 210 of the revision femoral component 200 may be curved in the medial-lateral direction in a manner similar to the posterior cam 110 of the primary femoral component 100 discussed above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthesis assembly comprising:
a tibial bearing configured to be coupled to a tibial tray, the tibial bearing having a platform and a spine extending upwardly from the platform, the spine having a posterior cam surface, the posterior cam surface including a concave cam surface and a convex cam surface: and
a first femoral component and a second femoral component, each of the first and second femoral components being configured to separately couple with the tibial bearing to articulate with the tibial bearing and including (i) a pair of spaced apart condyles defining an intracondylar notch therebetween and (ii) a posterior cam positioned in the intracondylar notch, the posterior cam including a posterior cam surface,
wherein the first femoral component includes an anterior surface positioned at an anterior end of the intracondylar notch such that the intracondylar notch includes an opening defined between the posterior cam and the anterior surface, and the posterior cam surface of the first femoral component includes a concave cam surface and a convex cam surface, the concave cam surface of the posterior cam being configured to initially contact the convex cam surface of the spine during a first range of flexion and the convex cam surface of the posterior cam being configured to initially contact the concave cam surface of the spine during a second range of flexion that is greater than the first range of flexion,
wherein the second femoral component includes an anterior cam that is connected to the posterior cam, and the posterior cam surface of the second femoral component is uniformly convex in the sagittal plane,
wherein the concave cam surface of the posterior cam surface of the first femoral component is concavely curved in the sagittal plane and the convex cam surface of the posterior cam surface of the first femoral component is convexly curved in the sagittal plane, and
wherein the first femoral component is a primary femoral component and the second femoral component is a revision femoral component.

2. The orthopaedic prosthesis assembly of claim 1, wherein the concave cam surface and the convex cam surface of the posterior cam surface of the first femoral component are concavely curved in a medial-lateral direction.

3. The orthopaedic prosthesis assembly of claim 2, wherein the posterior cam surface of the second femoral component is concavely curved in the medial-lateral direction.

4. The orthopaedic prosthesis assembly of claim 1, wherein the posterior cam surfaces of the first and second femoral components are each concavely curved in a medial-lateral direction.

5. The orthopaedic prosthesis assembly of claim 1, wherein the convex cam surface of the spine of the tibial bearing is convexly curved in the sagittal plane and the concave cam surface of the spine is concavely curved in the sagittal plane.

6. The orthopaedic prosthesis assembly of claim 5, wherein the concave cam surface and the convex cam surface of the spine are convexly curved in the transverse plane.

7. The orthopaedic prosthesis assembly of claim 6, wherein the concave cam surface of the spine has a radius of curvature in the transverse plane and the convex cam surface of the spine has a radius of curvature in the transverse plane that is substantially equal to the radius of curvature of the concave cam surface of the spine.

8. The orthopaedic prosthesis assembly of claim 1, wherein the convex cam surface of the spine of the tibial bearing is located superiorly relative to the concave cam surface of the spine.

9. The orthopaedic prosthesis assembly of claim 1, wherein the concave cam surface of the spine of the tibial bearing is defined by a first radius of curvature and the convex cam surface of the spine is defined by a second radius of curvature, the first radius of curvature being different from the second radius of curvature.

10. The orthopaedic prosthesis assembly of claim 9, wherein the concave cam surface of the posterior cam surface of the first femoral component is defined by a third radius of curvature and the convex cam surface of the posterior cam surface of the first femoral component is defined by a fourth radius of curvature, the third radius of curvature being different from the fourth radius of curvature.

11. A posterior stabilized knee orthopaedic prosthesis assembly comprising:
   a tibial bearing having (i) a platform including a medial bearing surface and a lateral bearing surface and (ii) a spine extending upwardly from the platform between the medial bearing surface and the lateral bearing surface, the spine including a posterior side having a superior cam surface and an inferior cam surface, wherein (i) the superior cam surface is convexly curved in the sagittal plane, (ii) the inferior cam surface is concavely curved in the sagittal plane, and (iii) the superior cam surface and the inferior cam surface are convexly curved in the transverse plane;
   a primary femoral component and a revision femoral component, each of the primary and revision femoral components being configured to separately couple with the tibial bearing and articulate on the tibial bearing during a range of flexion,
   wherein the primary femoral component includes (i) a primary lateral condyle configured to articulate with the lateral bearing surface of the tibial bearing, (ii) a primary medial condyle configured to articulate with the medial bearing surface, and (iii) a primary posterior cam positioned in a primary intracondylar notch defined between the primary lateral condyle and the primary medial condyle, the primary posterior cam including a primary concave cam surface and a primary convex cam surface, the primary concave cam surface being positioned to initially contact the superior cam surface of the spine at a first degree of flexion and the primary convex cam surface being positioned to initially contact the inferior cam surface of the spine at a second degree of flexion greater than the first degree of flexion,
   wherein the primary concave cam surface is concavely curved in the sagittal plane and the primary convex cam surface is convexly curved in the sagittal plane,
   wherein the revision femoral component includes (i) a revision lateral condyle configured to articulate with the lateral bearing surface of the tibial bearing, (ii) a revision medial condyle configured to articulate with the medial bearing surface, and (iii) a revision posterior cam positioned in a revision intracondylar notch defined between the revision lateral condyle and the revision medial condyle, the revision posterior cam including a revision convex cam surface, the revision convex cam surface being positioned to initially contact the superior cam surface of the spine at a third degree of flexion and initially contact the inferior cam surface of the spine at a fourth degree of flexion greater than the third degree of flexion,
   wherein the revision posterior cam is uniformly convexly curved in the sagittal plane.

* * * * *